(12) United States Patent
Sintov et al.

(10) Patent No.: US 6,274,166 B1
(45) Date of Patent: Aug. 14, 2001

(54) TRANSDERMAL DELIVERY SYSTEM

(75) Inventors: Amnon Sintov, Omer; Uri Wormser, Jerusalem, both of (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 0 days.

(21) Appl. No.: 09/424,525

(22) PCT Filed: May 4, 1998

(86) PCT No.: PCT/IL98/00205

§ 371 Date: Nov. 23, 1999

§ 102(e) Date: Nov. 23, 1999

(87) PCT Pub. No.: WO98/53847

PCT Pub. Date: Dec. 3, 1998

(30) Foreign Application Priority Data

May 29, 1997 (IL) .......................................... 120943

(51) Int. Cl.[7] ............................ A61F 13/00; A61F 13/02; A61L 15/16
(52) U.S. Cl. ............................ 424/449; 424/448; 424/443
(58) Field of Search ..................................... 424/449, 448; 514/2, 3, 5

(56) References Cited

U.S. PATENT DOCUMENTS 4,229,410 * 10/1980 Kosti ...................................... 422/28

FOREIGN PATENT DOCUMENTS

WO 85/05036 * 11/1985 (EP) ............................. A61K/37/36
WO 90/00899 * 2/1990 (EP) ............................. A61K/27/12
WO 90/01023 * 2/1990 (EP) ............................. C07C/99/02

OTHER PUBLICATIONS

Morgan, M.S. et al. "Participation of Cellular Thiol/Disulphide Groups on the Uptake, Degradation and Broactivity of Insulin in Primary Cultures of Rat Hepatocytes". Bio Medical Journal, vol. 2, pp.: 349–356, XP–002–077/48.*

* cited by examiner

Primary Examiner—Thurman K. Page
Assistant Examiner—Isis Ghali
(74) Attorney, Agent, or Firm—Leydig, Voit & Mayer, Ltd.

(57) ABSTRACT

A transdermal delivery system comprising an active ingredient selected from the group consisting of peptides, proteins and mixtures thereof and a pharmaceutically acceptable oxidizing agent. The transdermal delivery system is an easy-to-use topical system that facilitates the penetration of an active ingredient, such as insulin, through the skin layers and into the blood stream. Additionally, the invention includes a method for treating diabetes and other pathologic systemic conditions comprising administering an active ingredient selected from the group consisting of peptides, proteins and mixtures thereof and a pharmaceutically acceptable oxidizing agent.

5 Claims, 9 Drawing Sheets

Dermal Permeation of Human Insulin

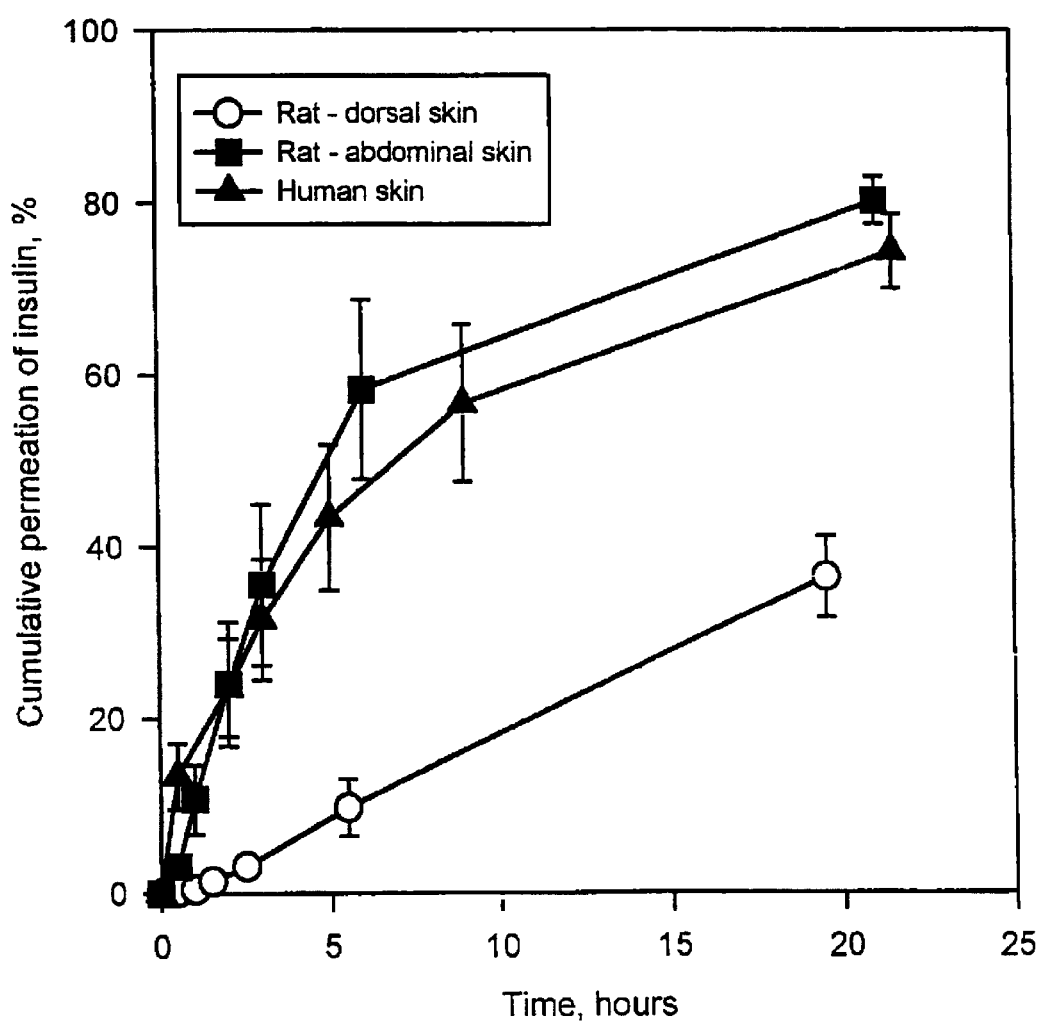

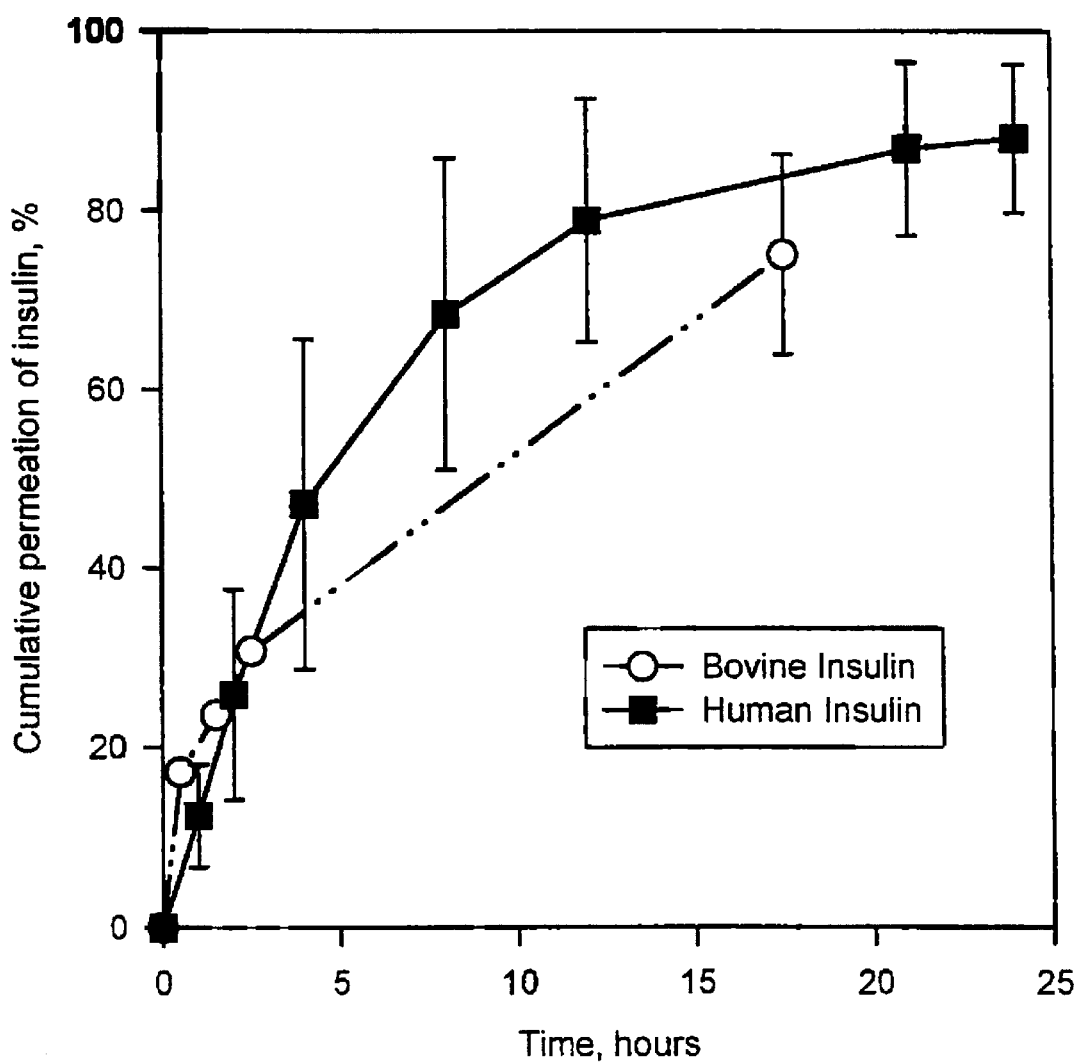

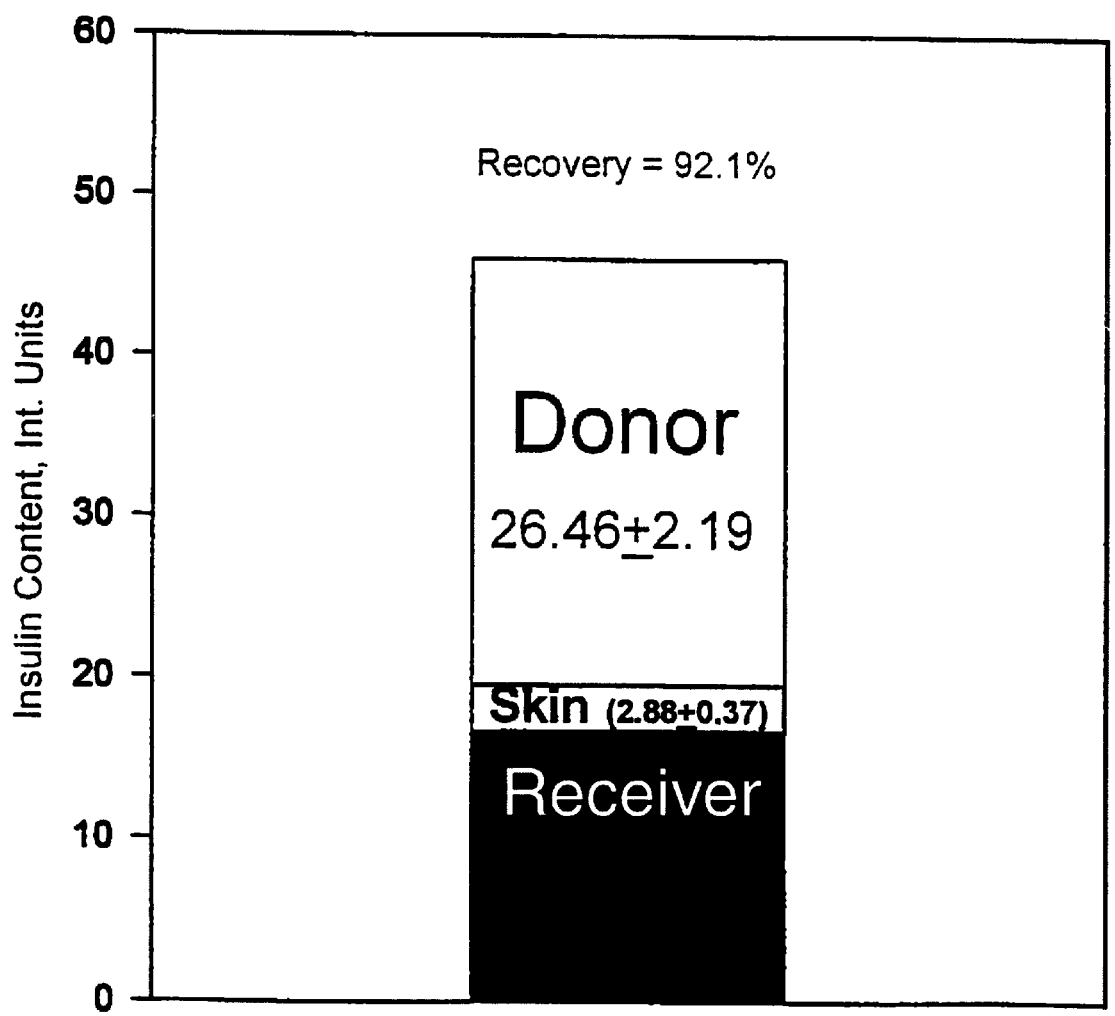

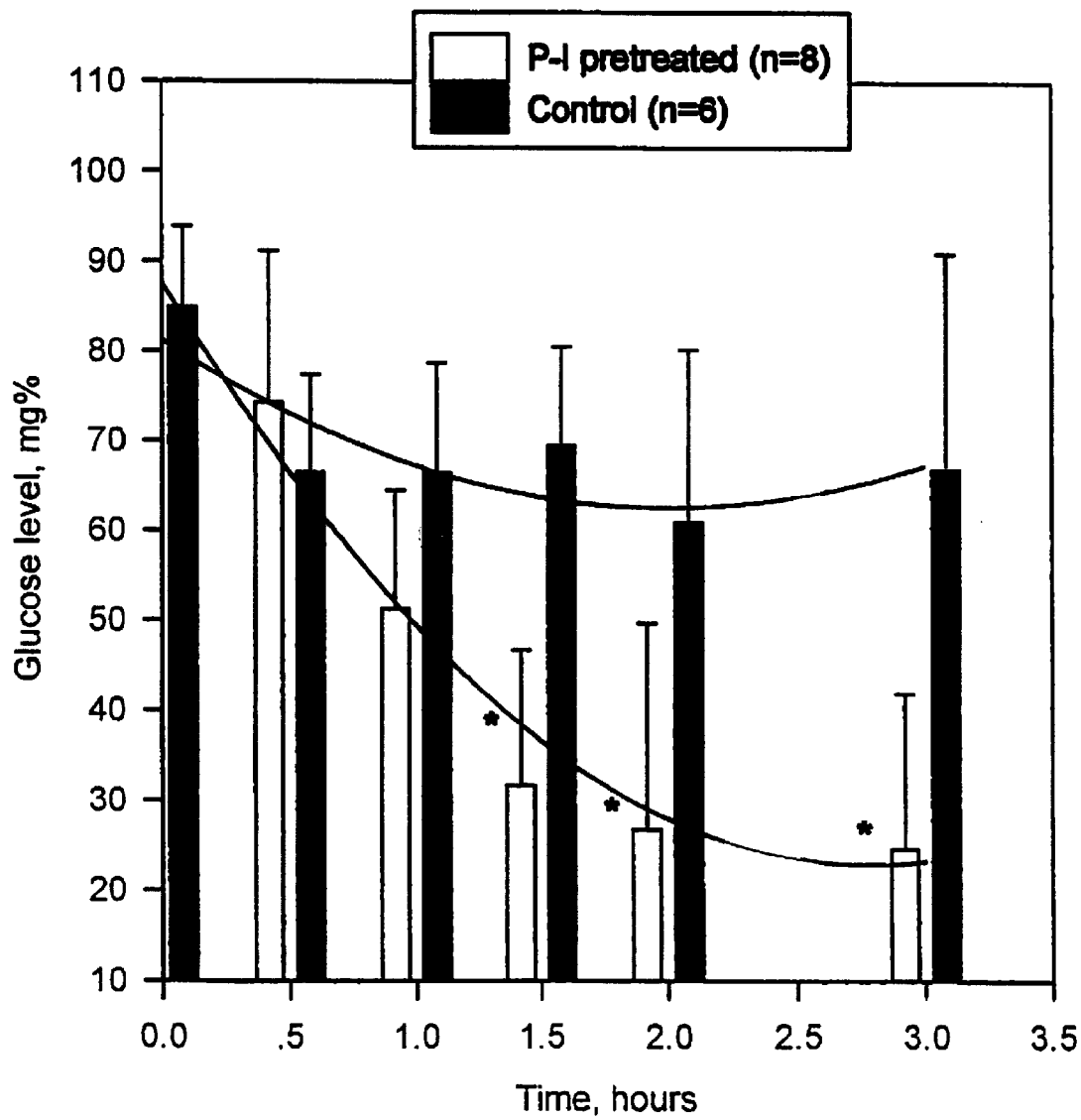

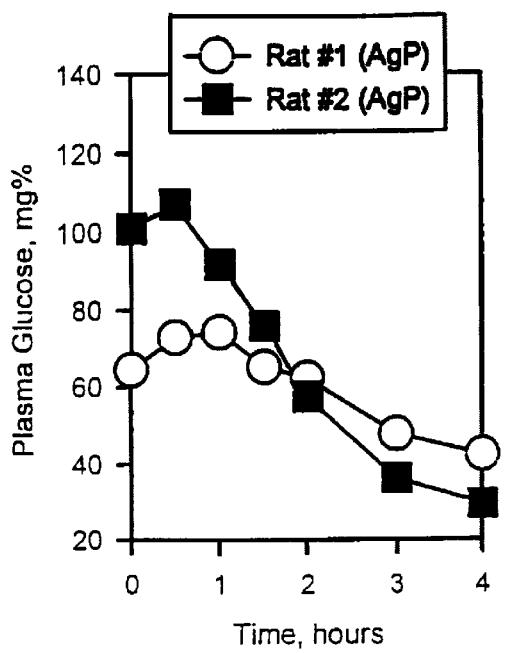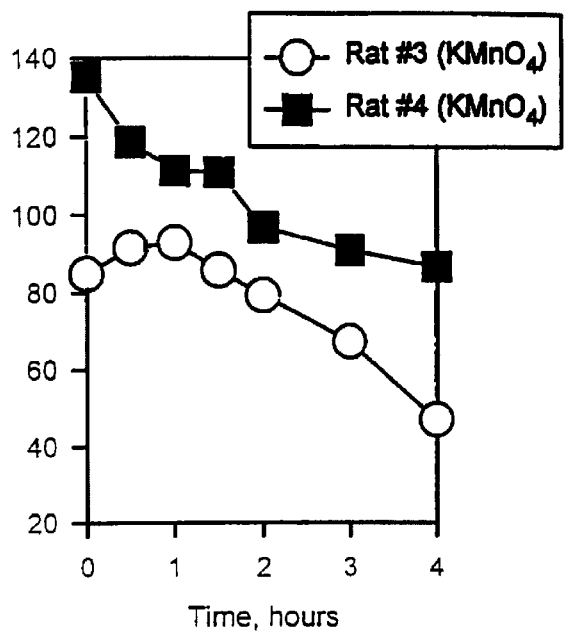
Fig. 5a
Fig. 5b
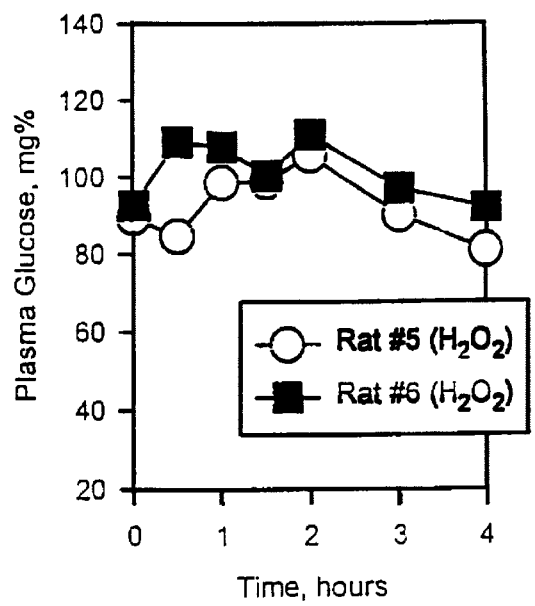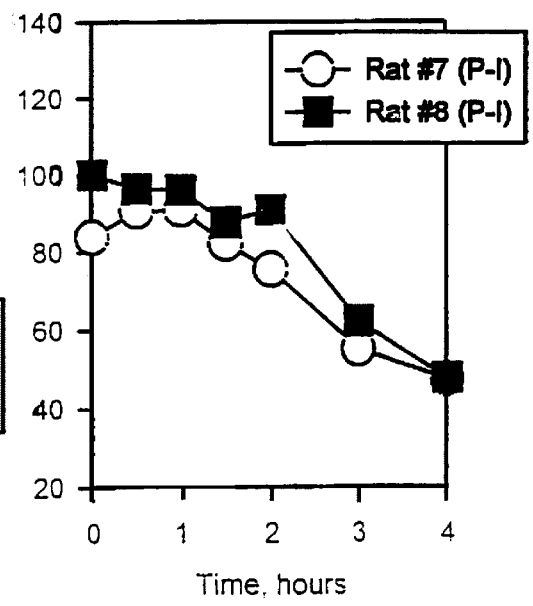
Fig. 5c
Fig. 5d

Effect of dermal application of insulin on plasma glucose levels of DEM-treated non-fasted rats

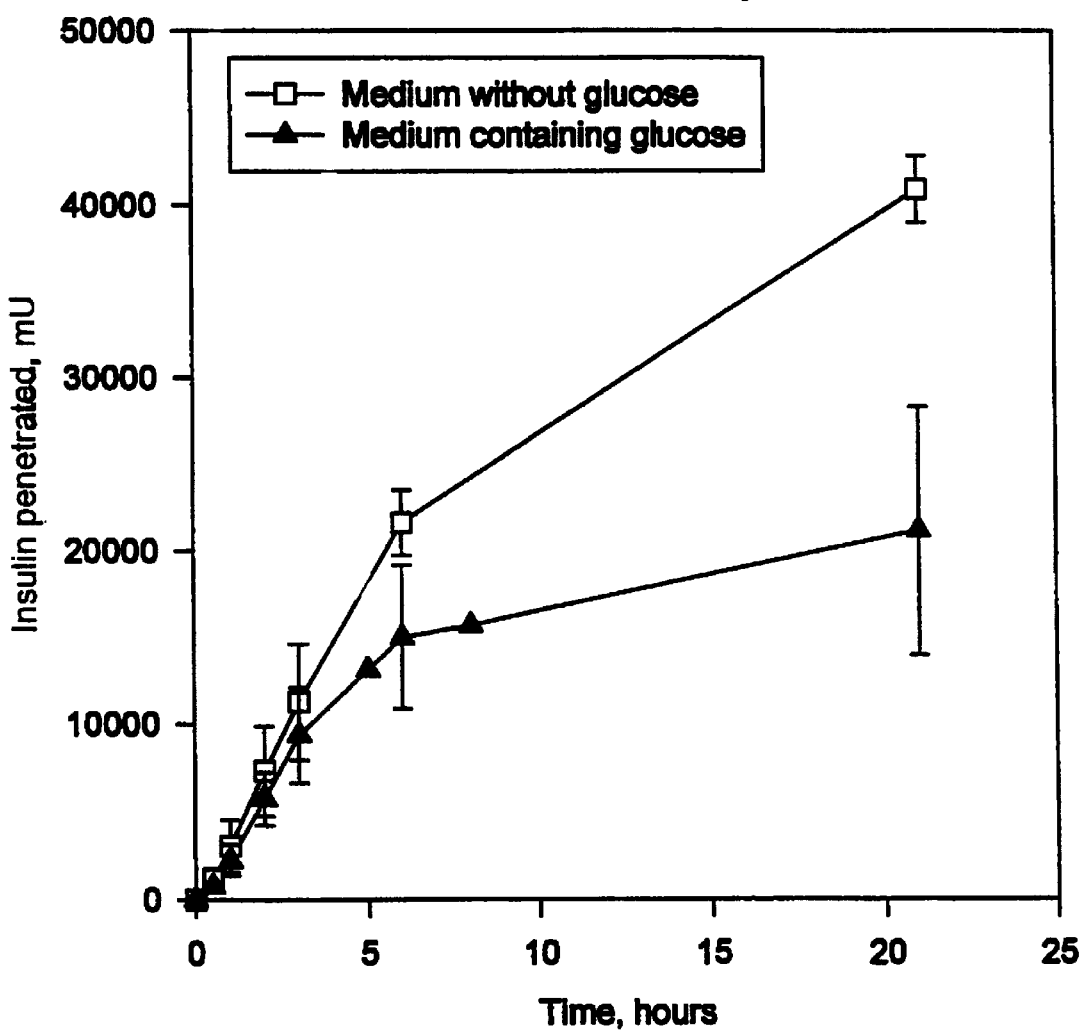

TRANSDERMAL DELIVERY SYSTEM

FIELD OF THE INVENTION

The present invention relates to a transdermal delivery system containing an active ingredient selected from the group consisting of peptides, proteins and mixtures thereof. More particularly the present invention provides systems and compositions which are pharmaceutically accepted and easy-to-use topical systems containing an active ingredient selected from the group consisting of peptides, proteins and mixtures thereof. These systems incorporate further components that assist in stabilizing the active material, e.g., by preventing the inactivation thereof and facilitating the penetration thereof as active molecules through the skin layers.

It has been discovered in the present invention that oxidizing agents such as iodine, potassium permanganate, peroxides and silver protein enable the application of formulations containing proteins and peptides and especially insulin onto the skin.

BACKGROUND ART

Insulin is secreted from beta cells of pancreatic Langerhans islet in its active form. The human insulin is composed of two polypeptides, the A and B chain, usually of 21 and 30 amino acids residues, respectively, with a molecular mass of about 5800 DA. The peptides are interconnected by disulfide bonds of the cysteine residues at A7–B7, A20–B19 and A6–A11. Insulin exerts a wide variety of biological activities including controlling the uptake, utilization, and storage of cellular nutrients such as glucose, amino acids and fatty acids. The important target tissues of insulin are liver, muscle and fat but many other cell types are also influenced by this hormone. [Davis, S N; Granner, D K (1996) In: Goodman & Gilman's The Pharmacological Basis of Therapeutics. ninth edition ed. (Eds: Hardman, J G et al.) McGraw-Hill, 1487—1517].

Diabetes and Insulin: One of the main physiological roles of insulin is stimulation of glucose transport into muscle and adipose tissues. A defect in this system leads to the diabetes mellitus syndrome characterized by hyperglycemia, changes in the metabolism of carbohydrates, lipids and proteins, and by elevated incidence of vascular disorders. There are two main diabetes, insulin-dependent diabetes mellitus (IDDM) with an incidence of 1–43 per 100,000 inhabitants in the Western countries, and the non-insulin-dependent diabetes mellitus (NIDDM) whose incidence is between 100–800 per 100,000 inhabitants in the Western countries (The above reference).

Insulin is the main treatment of all IDDM and many NIDDM patients. Long-term treatment is predominantly based on subcutaneous administration of insulin formulations. There are long-, short- and intermediate-acting preparation which are used according to the special requirements of the patient. However, apart from the discomfort and troublesome feelings and the possibility of infection associated with daily injections along the entire lifetime (particularly with IDDM, formerly termed juvenile-onset diabetes mellitus), this kind of therapy has serious clinical problems mainly with the maintenance of the appropriate blood levels of the hormone resulting in non-physiological blood glucose levels and other complications. Although much effort has been made in developing insulin analogs [Brange, J; et al. (1990) Diabetes 13, 923–954] and genetic engineering methodologies [Sutherland, DER et al. (1989) Diabetes 38 Suppl 1, 46–54], there are no successful findings for solving the clinical problems associated with parenteral insulin injections.

One of the approaches aimed to cope with the aforementioned difficulty was to deliver the hormone non-invasively, via transdermal route of administration. By this procedure, the annoyance and inconvenience of the parenteral injections can be avoided, moreover, much steadier blood hormone levels can be achieved due to prolonged delivery of the drug. Several low molecular weight drugs have been formulated and are being clinically used as transdermal preparations. However, apart from a few medicines, many drugs, particularly peptides and proteins, are not successfully formulated for transdermal delivery. In vitro experiments have shown that α-melanocyte stimulating hormone analog can penetrate across human and mouse, but cannot penetrate rat skin [Dawson, B V et al. (1990) J. Invest. Dermatol. 94, 432–435; Dawson, B V et al. (1988) Life. Sci. 43, 1111–1117] and that enkephaiin can penetrate hairless mouse skin but in the presence of the enhancer n-decylmethyl sulfoxide and proteinase inhibitors [Choi, H K et al. (1990) Pharm. Res. 7, 1099–1106]. However, apart from one study with small number of mice which showed reduced levels of blood glucose after 4 hours of cutaneous application of insulin with enhancer [Liedtke, R K et al. (1990) Drug Res. 40, 880–883], no efficient in vivo transdermal penetration of peptides and proteins, by chemical means (e.g. enhancer or proteinase inhibitors) have been published. Transdermal penetration of various peptides and proteins can be enhanced by iontophoresis using electrical current for delivering charged agents across the skin. Various peptides and small proteins including insulin, calcitonin, vasopressin, luteinizing hormone-releasing hormone, (LHRH) leuprolide, thyrotropin-releasing hormone and cholecystokinin were tested in in vitro iontophoresis assays and some of them also in in vivo systems [Heit, M C et al. (1993) J Pharm Sci 1993 82(3):240–243; Srinivasan, V et al. (1990) J. Pharm. Sci. 79, 588–591; Burnette, R R and Marrero, D (1986) J. Pharm. Sci. 75, 738–743; Banga, A K and Chien, Y W (1993): Pharm. Res. 10, 697–702; Mao, X M et al. (1995) Yao. Hsueh. Hsueh. Pao. 30, 302–306; Mao, X M et al. (1995) Yao. Hsueh. Hsueh. Pao. 30, 881–885; Meyer, B R et al. (1989) Am. J. Med. Sci. 297, 321–325]. Additional technique to facilitate transdermal delivery of insulin by ultrasound vibration, termed sonophoresis, was used in both in vitro and in vivo systems [Tachibana, K and Tachibana, S (1991): J. Pharm. Pharmacol. 43, 270–271; Tachibana, K (1992) Pharm. Res. 9, 952–954; Mitragotri, S et al. (1995) Science. 269(5225), 850–853]. Although transdermal penetration of insulin and other proteins and peptides was enhanced by the sonophoretic and iontophoretic techniques, these procedures require complicated and an uneasy way of operation. Furthermore, the safety of long-term, daily use of this techniques was not confirmed. The fact that only one report, describing unsatisfactory results on the use of penetration enhancer in type II diabetic patients [Liedtke, R K et al. (1990): Drug Res. 40, 884–886] has been published, indicates the problematic issues of the above methods.

DISCLOSURE OF THE INVENTION

According to the present invention there is now provided a transdermal delivery system comprising an active ingredient selected from the group consisting of peptides, proteins and mixtures thereof and a pharmaceutically acceptable oxidizing agent.

As will be discussed hereinafter it is believed that said oxidizing agent serves to oxidize reduced glutathione thereby preventing it functioning as an inactivating agent.

Assuming that this hypothesis is correct then also a component such as buthionine sulfoximine which also prevent the formation of glutathione can be used in the present invention alone or in combination with an oxidizing agent to achieve the desired effect.

In preferred embodiments of the present invention said active ingredient is insulin.

A first series of experiments, using the in vitro Franz Cells, showed that insulin penetrates skin of several species including the rat, hairless mouse and human. However, in the parallel in vivo system, employing the insulin-containing well on rat abdominal skin, no reduction in blood glucose levels was observed. The in vivo/in vitro discrepancy may be associated with the ability of reduced glutathione (GSH) (and of other cellular SH groups) to inactivate insulin by reducing its disulfide bond(s) [Rafter, G W (1990) Biochem. Int. 20, 817–820] followed by aggregation of several peptide molecules via random production of disulfide bonds in the in vivo system. However, the in vitro system, after skin being dissected may suffer from cellular energy depletion i.e. reduced levels of NADPH. This is a key cofactor for glutathione reductase activity, which converts oxidized glutathione (GSSG) to the active reduced glutathione (GSH). NADPH depletion reduces GSH levels, consequently, insulin may not be inactivated by skin cells, resulting in its penetration into the circulatory system.

Confirmation of this hypothesis was obtained from the fact that addition of energy source such as glucose to the medium of the in vitro Franz cells resulted in reduced penetration of insulin. However, the opposite situation occurs in the in vivo system, i.e. the effect of high levels of GSH (and other SH groups), could be overcome by topical pretreatment of the skin with oxidizing agents (such as povidone iodine and silver protein), resulting in oxidation of the cellular GSH (and other R-SH groups) to form the inactive GSSG (and/or R-SS-R). Reduced levels of the former prevents inactivation of insulin, enabling hormone penetration via skin into the blood stream and reduction in blood glucose levels.

All tested oxidants resulted in time-dependent reduction in blood glucose levels, whereas rats without such pretreatment or treatment failed to show this phenomenon.

Povidone iodine (PI) (polyvinylpyrrolidone-iodine complex) ointment is widely used as an antiseptic agent. The successful combination of being safe and non-irritant as well as an efficient antiseptic agent was already demonstrated 40 years ago [Shelanski, H A and Shelanski, M V (1956) J. Int. Coll. Surg. 25, 727–734]. The fact that PI is commonly employed in hospitals, clinics and home use is further corroboration for its advantageous properties. Other oxidants such as silver protein (mild or strong) and permanganates, have been used for many years may also be employed in the compositions of this invention.

In the practice of this invention topical proteins such as insulin in therapeutically effective doses are incorporated into pharmaceutically acceptable carriers such as gels, ointments, solutions, paste, powder, and adhesive patch. The resulting formulations are applied to the skin of patients as many applications as needed, preferably once a day. The novel carriers contain insulin or other protein drugs that are not stable in vital skin in-vivo, thus need a protecting agent against skin biotransformation before approaching the systemic blood. The present invention comes to challenge the prior art, which considers the skin as a physical barrier to proteins such as insulin. It has been clearly proved that 5807-dalton human insulin quantitatively penetrates an excised skin in-vitro and in-vivo, but is inactivated through the in-vivo transport. This inactivation can be diminished by using oxidants such as povidone-iodine or silver protein. It has been hypothesized that these mild oxidizing agents result in a reduction in skin levels of glutathione and other reducing agents, thus preventing insulin inactivation caused by dimerization, aggregation, cleavage to two separate chains, cleavage of one s-s bond, etc.

The invention is derived, in part, from the discovery that the delivery of topically-applied protein drugs into the blood circulation is possible only if oxidizing agents are involved before or during the application.

The present invention relates to transdermal delivery of peptide/protein drugs and especially those having an s-s bond. The preferred compositions comprise a safe and effective quantities of: (a) a therapeutic protein/peptide, (b) an oxidant such as iodine or silver protein or combinations of such oxidants, (c) an appropriate vehicle system which may contain skin penetration enhancers selected from those known in the art. (see, e. g., Chien Y. W. Transdermal Controlled Systemic Medication, 1987 Marcel & Decker pgs. 83–90).

Effective levels of protein drugs are delivered by the novel compositions. An "effective" level is meant that a concentration of a drug is high enough to be effective in treating the condition in which the drug has been designed to treat. Examples of protein drugs are: insulin, alpha-, beta-, and gamma-interferon, human growth hormone alpha- and beta-1-transforming growth factor, granulocyte colony stimulating factor (G-CSF), granulocyte macrophage colony stimulating factor (G-MCSF), Parathyroid hormone (PTH), human or salmon calcitonin, glucagon, somatostatin, vasoactive intestinal peptide (VIP) and LHRH analogs.

In addition to the preferred use of iodine and silver protein, other oxidants can be used alone or in combinations. For example, potassium permanganate, hydrogen peroxide, benzoyl peroxide, urea peroxide, ferric and cupric salts, active oxygen, and sodium peroxyborate can be selected according to their effectiveness in protecting and delivering the peptide drugs across the skin. As mentioned above, povidone-iodine and silver protein are preferably selected as safe and effective "skin-protein-stabilizer" in a pretreatment procedure or in treatment composition at concentrations of 0.01% to 80%.

The therapeutic proteins and its protectors/stabilizers in-vivo, can be applied as a topical formulation such as cream (o/w or w/o), ointment, film-forming liquid spray, or gel using occlusive or non-occlusive dressings. A composition in an appropriate polymeric patch is preferable as transdermal protein delivery, and it consists of compatible adhesive polymers known in the art. The polymer can be selected from the group of acrylic polymers, cellulosic polymers, polyurethanes, polylactic/polyglycolic acids, polyamino acids, polysaccharides, polyurea, polyvinyl alcohol, polyvinylpyrrolidone (povidone), and natural proteins.

A transdermal patch can consist several layers: in the inner side a peelable plastic cover will protect the drug layer containing the adhesive polymer, plasticizer, the oxidizing agents, penetration enhancers and other excipients. The outer layers (i.e., the external layers) are designated to protect the drug from diffusion outward and to stick the patch by its margins to the skin, so the drug layer is occluded from all sides except the skin side where it is in close contact. (see, e.g., Chien Y. W. Transdermal Controlled Systemic Medication, 1987 Marcel & Decker pgs. 93–120, 365–378).

While the invention will now be described in connection with certain preferred embodiments in the following examples and with reference to the accompanying figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

BRIEF DESCRIPTION OF THE DRAWINGS

In the drawings:

FIG. 1. is a graphic representation of dermal permeation of human insulin;

FIG. 2 is a graphic representation of insulin transport through hairless mouse skin;

FIG. 3 is a graphic representation of insulin partitioning through rat skin;

FIG. 4 is a graphic representation of the effect of dermally applied insulin on plasma glucose levels;

FIGS. 5a–5d are graphic representations of the effect of various oxidants on transdermal insulin delivery as evaluated by plasma glucose levels;

FIG. 9 is a graphic representation of cutaneous permeation of human insulin.

DESCRIPTION OF PREFERRED EMBODIMENTS

EXAMPLE 1

Figure 6:
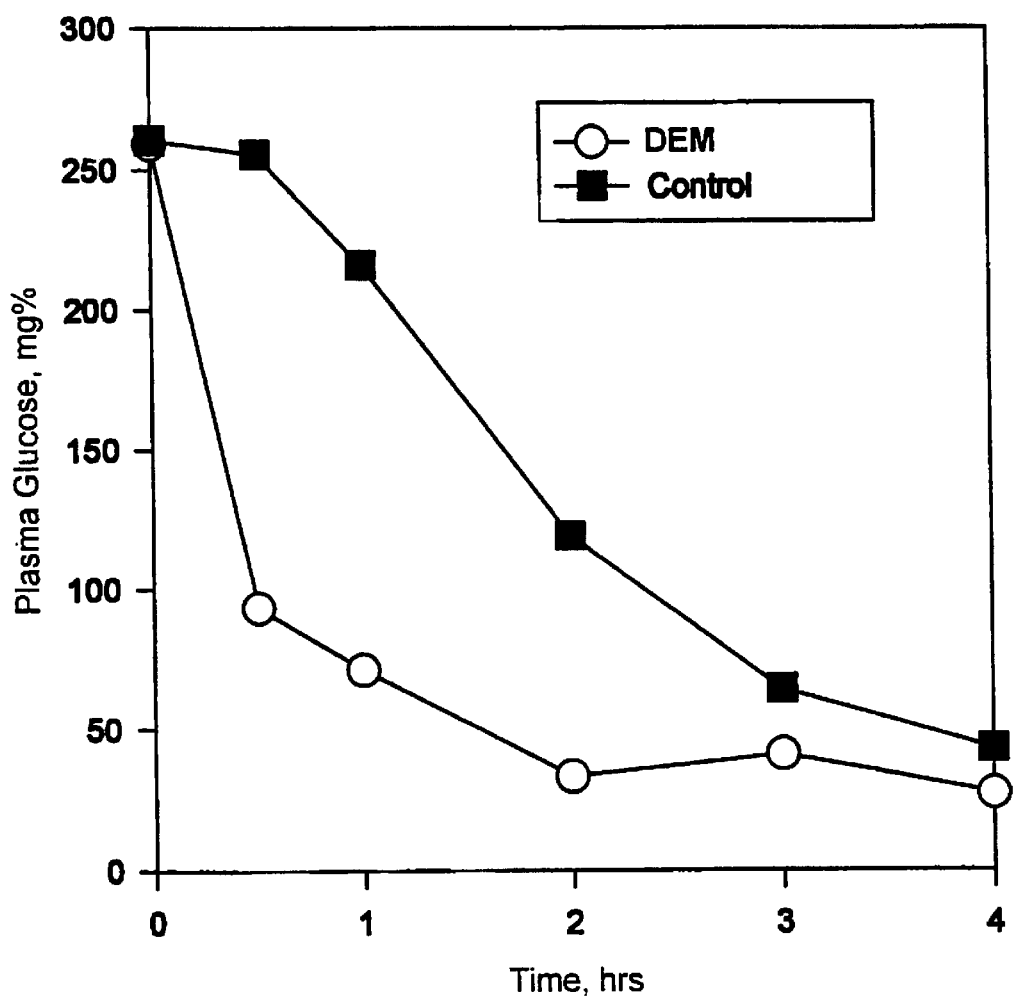
FIG. 6 is a graphic representation of the effect of dermal application of insulin on plasma glucose levels of DEM-treated non-fasted rats.

A pharmaceutical formulation for transdermal purpose, containing silver protein:

| Composition | |
|---|---|
| Insulin | 50 IU |
| Silver protein | 0.025 g |
| Water | 0.5 ml |

EXAMPLE 2

A pharmaceutical formulation for transdermal purpose, containing a penetration enhancer, administered after skin has been pretreated with povidone-iodine:

| | |
|---|---|
| Povidone - Iodine USP ointment | 0.5 g |
| Composition of insulin formula | |
| Insulin | 50 IU |
| Oleic acid | 15 mg |
| Propylene glycol | 150 mg |
| Water | 1 ml |
| adjust pH to: | 7.5–7.9 |

EXAMPLE 3

A pharmaceutical formulation for transdermal purpose, containing silver protein and a penetration enhancer, administered after skin has been pretreated with povidone-iodine:

| | |
|---|---|
| Povidone - Iodine USP ointment | 0.5 g |
| Composition of insulin formula | |
| Insulin | 50 IU |
| Silver protein | 25 mg |
| Oleic acid | 15 mg |
| Propylene glycol | 150 mg |
| Water | 1 ml |
| adjust pH to: | 7.5–7.9 |

COMPARATIVE EXAMPLE 4

In-Vitro Skin Penetration of Insulin

Diffusion cells: The permeation of insulin through various sources of skin was measured in-vitro using Franz diffusion cell system. The diffusion area was 1.767 $cm^2$ (15 mm diameter orifice), and the receptor compartment volumes varied between 11.8 to 12.4 ml. The solutions in the receiver side were stirred by externally driven, teflon-coated magnetic bars.

Skin preparation: Full-thickness skin was excised from the fresh carcasses of animals (CD1 hairless mice, and Sprague-Dawley rats) sacrificed with ethyl ether. Subcutaneous fat was removed with scalpel and the skin was mounted in diffusion cells (n=6 for each experiment). The abdominal skin was cut and placed with the stratum corneum facing up on the receiver chambers, then donor chambers were clamped. The excess skin was trimmed off and the receiver chamber, defined as the side facing the dermis, was filled with 0.05 M phosphate buffer or PBS (pH=7.4). Human skin was obtained from Plastic Surgery department, Soroka Hospital, Beer-Sheva.

Permeation: After 30 minutes of the skin washing performed at 37° C., the buffer was removed from the cells. Aliquots of 0.5 ml Humulin R (human insulin 100 IU/ml Injection, Eli Lilly&Co., Fegersheim, France) or bovine insulin (2 mg/ml solution, Fluka, Switzerland) were accurately pippeted on the skin in the donor compartments, and phosphate buffer was filled in the receiver sides. Samples (2 ml) were withdrawn from the receiver solution at predetermined time intervals and the cells were replenished to their marked volumes with a fresh buffer solution. Careful addition of solution into the receiver compartment was taken place in order to avoid air trapping beneath the dermis.

Calculations: As a result of large volume sampling from the receiver solution and replacing with equal volumes, the solution was constantly diluted. taking this into account, cumulative drug permeation ($Q_t$) was calculated from the following equation:

$$Q_t = V_r C_t + \sum_{i=0}^{t-1} V_s C_i$$

where $C_t$ is the drug concentration in the receiver solution at each sampling time point, $C_i$ is the drug concentration of the i-th sample and $V_r$ and $V_s$ are volumes of the receiver solution and the sample, respectively. Data were expressed as the cumulative permeation ($Q_t$) in percent of applied insulin over the given skin surface area (S=1.767 cm²).

Insulin recovery test: Rat abdominal skin was excised after hair had been clipped off, and mounted on 4 diffusion cells containing phosphate buffer (pH=7.4) in the receiver chamber. Humulin R (0.5 ml, 50 IU) was applied in the donor compartment, and after 3-hour diffusion the receiver and the donor solutions were sampled. The skin was rinsed carefully with phosphate buffer, and extracted with 2×1 ml ethanol. The extracts and the sampling solutions were analyzed for insulin as described below.

HPLC analysis of insulin: Aliquots of 10 ml from each vial were injected into the HPLC system, which was equipped with a prepacked $C_{18}$ column (Lichrospher 60 RP-select B, 5 mm, 125×4 mm). The detection of insulin was carried out at 270 nm. The samples were chromatographed using an isocratic mobile phase consisting of acetonitrile—0.1% trifluoroacetic acid (ratio: 3:7). A flow rate of 1 ml/min was used. The data was analyzed using standard solutions at two different concentrations which were run for every series of chromatographed samples. Plots of calibration curve [peak area versus drug concentration] over the range of 0.125–2.5 IU/ml were linear.

Results: FIG. 1 shows the in-vitro cumulative penetration profiles (fluxes across the skin) of human insulin through rat abdominal and dorsal skin compared to the transport across human skin. The difference in penetration observed between the dorsal skin and the abdominal one is apparently because dorsal skin is about 5 times thicker. It is important to note that human skin permeability to insulin is quite equivalent to the permeability of the abdominal skin of the rat. FIG. 2 presents a similar penetration of insulin from two origins (recombinant human and bovine) through hairless mouse skin. By looking in both Figures and also in Table I, we have impressed that insulin can penetrate quantitatively and with almost full recovery. FIG. 3 shows that 92.1% of intact insulin is recovered from the in-vitro permeation procedure with 33.42% and 5.76% of the drug accumulates in the receptor and the skin, respectively, after only 3 hours. These findings raise a large question mark why insulin is allegedly "impermeable" in-vivo into the circulation as reported in the literature (see background).

TABLE I

Determination of insulin in both receiver and donor compartments after about 20 hours of in-vitro diffusion through skin

| Origin of skin | Insulin | Time of analysis, hours | Insulin recovered | % of total |
|---|---|---|---|---|
| Hairless mouse | Bovine | 17.5 | 1057.7 ± 159.2 mg | 105.8 ± 15.9 |
| Hairless mouse | Human | 24 | 41.40 ± 2.80 IU | 82.8 ± 5.6 |
| Rat - abdominal | Human | 21 | 42.07 ± 0.52 IU | 84.1 ± 1.0 |
| Rat - dorsal | Human | 19.5 | 35.46 ± 2.07 IU | 70.9 ± 4.1 |
| Human | Human | 21.5 | 38.50 ± 2.30 IU | 85.5 ± 5.1 |

COMPARATIVE EXAMPLE 5

In-vivo Evaluation of Dermally-applied Insulin and Povidone-iodine

Animals: Locally-grown rats (Sprague-Dawley strain) were anesthetized after overnight fast (15 mg/ml pentobarbital sodium, 0.2–0.3 ml i.p.). The rats were placed on their back, the abdominal hair was trimmed off, then the skin was washed gently with distilled water. The animals were maintained with 0.1 ml pentobarbital 15 mg/ml solution to keep them continuously asleep during the experiment.

Insulin application: Small cylinders (13 mm diameter orifice) were attached on the central part of the rat abdomen by a silicon glue. Doses of 0.5 ml of Humulin R solution for injection (equivalent to 50 IU human insulin) were pippeted into the open cylinders. In some experiments insulin solution contained other ingredients such as penetration enhancers (i.e., sodium oleate, propylene glycol) or an oxidant (i.e., mild silver protein BPC—Argirol, Givaudan, France). Careful attention was paid that the liquid has covered the entire skin area in the cylinder and that no leaking has occurred.

Pretreatment: Before insulin application (in cases where a combined treatment was not studied), the skin was treated with antioxidants by spreading of povidone-iodine ointment (PI, Polydine—Fischer, Israel) for 0.5–3 hours, or was exposed to an oxidant in aqueous solution using the above cylinder attachment procedure.

Blood sampling and plasma glucose monitoring: Blood samples (ca. 200 ml) were taken from the tail vein into 0.5-ml tubes containing 5 ml heparin solution (5000 i.u./ml, Laboratoire Choay, France). The tubes were centrifuged (5000 rpm, 5 minutes), and 10 ml of separated plasma was transferred with 1 ml of GOD/PAP reagent solution (Glucose PAP kit, Hoffman-La Roche, basel, Switzerland). The absorbance of developed color was read measured at 500 nm wavelength, against blank and an appropriate calibration curve.

Results: FIG. 4 demonstrates the first evidence for the essence of this invention. It has been definitely shown that in an in-vivo experiment, a pretreatment with an oxidizing agent, Povidone-Iodine (PI) ointment, insulin application on the skin produces a significant reduction in plasma glucose levels. For comparison, plasma levels in control animals which were not treated with PI, were not influenced by dermal insulin. Surprisingly, Table II below present no difference between groups in the quantity of insulin penetrated to the body. This supports the above in-vitro studies which clearly indicate on fluent insulin permeation through the skin. As already described in the background section, it has been surprisingly found according to this invention that the skin is not a physical barrier for insulin and other polypeptides. It seems that protein metabolism or biotransformation occurs in the skin during transport of the molecules. It has been proved that this biotransformation occurs only in live animals and not in excised skin tissues, no matter how fresh they are.

TABLE II

Insulin remained on the skin after 3 hours of in-vivo penetration

| PI treated rats | Remaining insulin (IU) | Control (non-PI) rats | Remaining insulin (IU) |
|---|---|---|---|
| 1 | 8.20 | 6 | 8.18 |
| 2 | 7.42 | 7 | 8.71 |
| 3 | 8.28 | 8 | 7.94 |
| 4 | 8.81 | 9 | 7.37 |
| 5 | 6.96 | 10 | 7.84 |
| Mean ± S.D.: | 7.94 ± 0.74 | Mean ± S.D.: | 8.00 ± 0.49 |
| % of dose: | 15.9% ± 1.5% | % of dose: | 16.0% ± 1.0% |

COMPARATIVE EXAMPLE 6

In-vivo Evaluation of Dermally-applied Insulin and Various Oxidants

Eight (8) locally-grown rats (Sprague-Dawley strain) were anesthetized after overnight fast (15 mg/ml pentobarbital sodium, 0.2–0.3 ml i.p.). The rats were placed on their back, the abdominal hair was trimmed off, then the skin was washed gently with distilled water. The animals were maintained with 0.1 ml pentobarbital 15 mg/ml solution to keep them continuously asleep during the experiment. In 6 of the rats, small cylinders (13 mm diameter orifice) were attached on the central part of the rat abdomen by a silicon glue. The cylinders were filled with aqueous aliquots (0.5 ml) of oxidizing agents—2 cylinders with 5% silver protein solution, 2 cylinders with 0.01% potassium permanganate, and 2 cylinders with 9% hydrogen peroxide. The two remaining animals were pretreated with povidone-iodine as already described in example 5. After 3 hours, the cylinders were emptied or the iodine was washed out of the skin, then doses of 0.5 ml of Humulin R solution for injection (equivalent to 50 IU human insulin) were pippeted into the open cylinders.

Blood sampling and glucose measurement were performed as described in example 5.

Results: FIG. 5 presents the effectiveness of the four oxidants in facilitating plasma glucose reduction by dermally-applied insulin. It can be seen that glucose levels reduced significantly in silver protein, $KMnO_4$, and povidone-iodine pretreated rats. No glucose reduction occurred in rats pretreated with 9% hydrogen peroxide solution, probably because peroxides are sensitive to peroxidase and catalase enzymatic reactions. If peroxides are selected, less sensitive and long lasting compounds should be used (i.e., carbamide peroxide) for this purpose.

COMPARATIVE EXAMPLE 7

In-vivo Evaluation of Dermally-applied Insulin After Diethyl Maleate (DEM) Pretreatment Two non-fasted locally-grown rats (Sprague-Dawley strain) were anesthetized (15 mg/ml pentobarbital sodium, 0.2–0.3 ml i.p.). The rats were placed on their back, the abdominal hair was trimmed off, then the skin was washed gently with distilled water. The animals were maintained with 0.1 ml pentobarbital 15 mg/ml solution to keep them continuously asleep during the experiment. Diethyl maleate, a glutathion depleting agent, was injected intraperitoneally (0.5 ml, 20% v/v ethanolic solution) to one rat only. Small cylinders (13 mm diameter orifice) were attached on the central part of the rat abdomen by a silicon glue. The cylinders were filled with aqueous aliquots (0.5 ml) of Humulin R solution for injection (equivalent to 50 IU human insulin).

Blood sampling and glucose measurement were performed as described in example 5.

Results: FIG. 6 shows the abrupt reduction of plasma glucose in the DEM-treated rat formed by the skin transport of active insulin. In comparison, the plasma glucose in the untreated rat decreased relatively slower, a reduction that was driven by endogenous insulin in the fasted state.

COMPARATIVE EXAMPLE 8

In-vivo Evaluation of Dermally-applied Insulin co-administered with Silver Protein, Following Pretreatment with Povidone-iodine Six (6) locally-grown rats (Sprague-Dawley strain) were anesthetized after overnight fast (15 mg/ml pentobarbital sodium, 0.2–0.3 ml i.p.). The rats were placed on their back, the abdominal hair was trimmed off, then the skin was washed gently with distilled water. The animals were maintained with 0.1 ml pentobarbital 15 mg/ml solution to keep them continuously asleep during the experiment. Three of the animals were used as untreated control group, while the rest were pretreated with povidone-iodine ointment as described in example 5, except that only 30-min application was performed instead of 3 hours. After the ointment was gently washed out, small cylinders (13 mm diameter orifice) were attached on the central part of the rat abdomen by a silicon glue. The cylinders were filled with 0.5 ml of Humulin R solution for injection (equivalent to 50 IU human insulin) in the control group, and 0.5 ml Humulin R solution containing 5% silver protein in the treatment group.

Blood sampling and glucose measurement were performed as described in example 5.

Figure 7A:
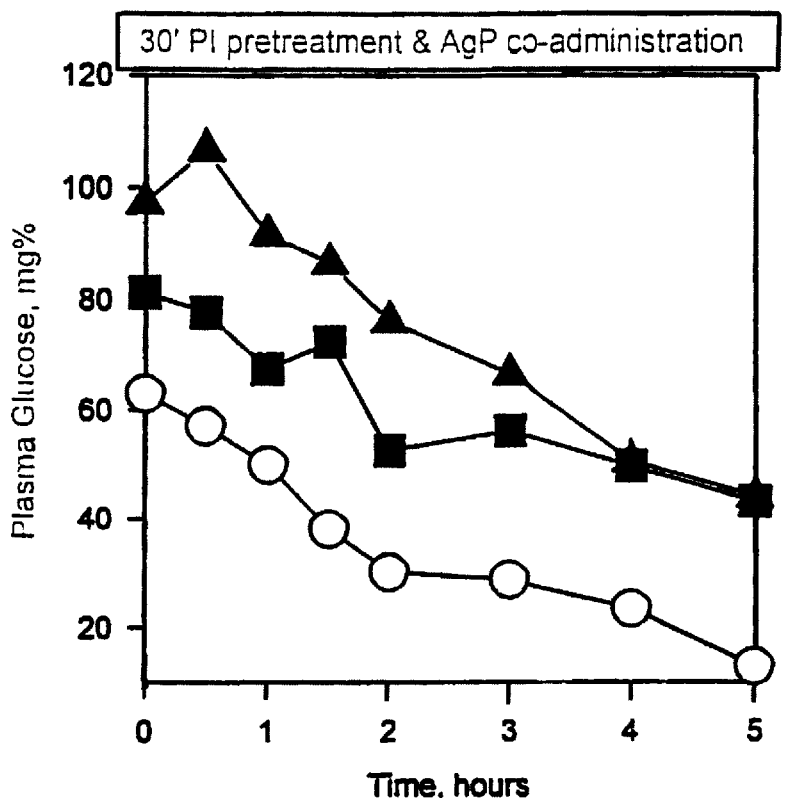
FIGS. 7a and 7b are graphic representations of optimized treatment for dermal insulin as compared to the untreated control.
Figure 7B:
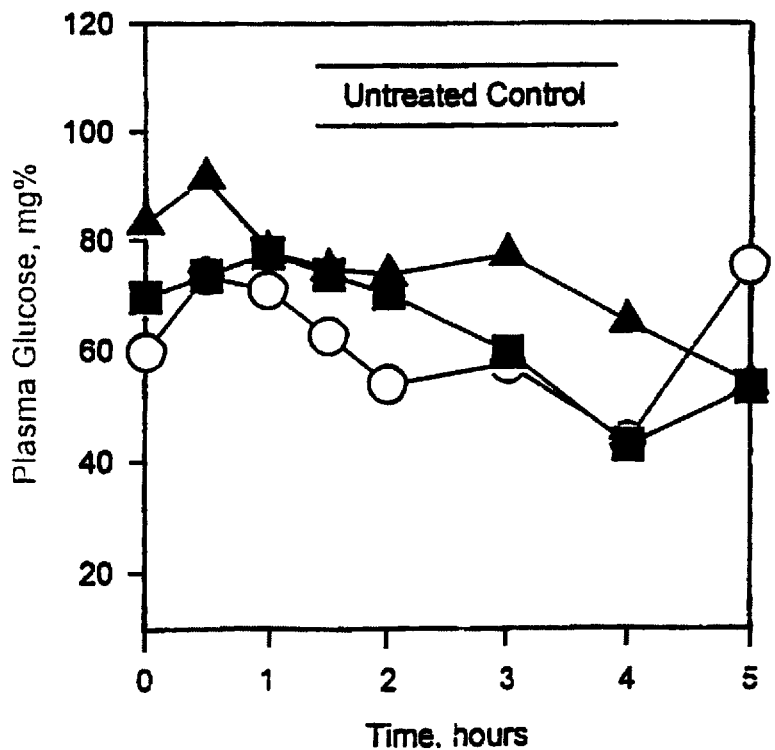

Results: FIG. 7 presents the effectiveness of the treatment in facilitating plasma glucose reduction by the dermally-applied insulin. As it is shown in the Figure, a consistent reduction rate in glucose levels was monitored in the treated rats, while the untreated rats demonstrated almost the same levels with no change.

COMPARATIVE EXAMPLE 9

In-vivo Evaluation of Dermally-applied Insulin and Povidone-iodine

This experiment used the same protocol as in example 5 and this is actually a repetition of the study aimed to examine the contribution of povidone-iodine in delivering unchanged and active insulin transdermally.

Figure 8A:
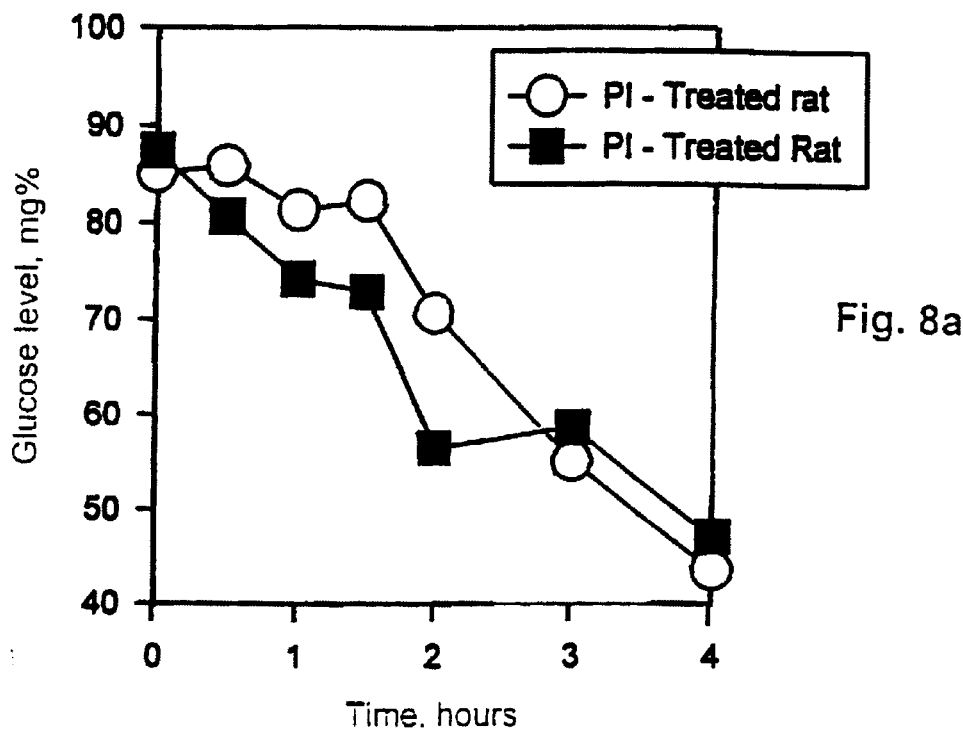
FIGS. 8a and 8b are graphic representations of optimization of dermal insulin treatment as compared to untreated control rats.
Figure 8B:
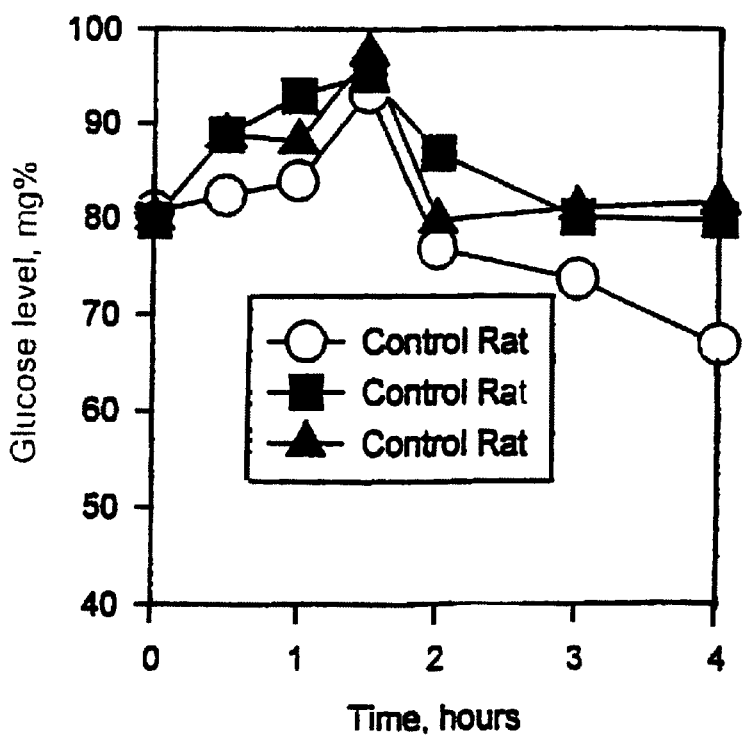

Results: FIG. 8 presents the effectiveness of the P-I pretreatment in facilitating plasma glucose reduction by dermally-applied insulin. While no change occurred in the control rats, plasma glucose decreased significantly in the P-I treated animals.

COMPARATIVE EXAMPLE 10

In-Vitro Skin Penetration of Insulin—Influence of glucose

The use of glucose in the receiver chamber of the Franz diffusion cells may provide the energy needed to convert oxidized glutathion to its reduced form in the non-blood perfused skin. This experiment was made in an attempt to imitate the in-vivo situation, and to elaborate some indication for the possible mechanism in which insulin is inactivated in skin.

The in-vitro procedure was performed as described in example 4 by the same protocol, except that 100 mg % glucose in buffer solution was placed in the receiver chambers of assigned cells. Cells containing buffer alone were used as control.

Results: FIG. 9 shows the significant difference observed between the penetration profiles of insulin through skin exposed to glucose and skin exposed to buffer only. The decrease in insulin skin permeation in glucose containing cells, indicates that insulin can undergo glucose-dependent biodegradation or transformation in the skin.

This example together with example 7 imply on the presence of significant levels of reducing agents such as reduced glutathion in the vital skin that are responsible for insulin inactivation during its transport to systemic blood. These reducing agents can be oxidized by oxidants according to the scope and the novel findings of the present invention, thus facilitate the transdermal delivery of active insulin.

COMPARATIVE EXAMPLE 11

In-vivo Skin Uptake of Dermally-applied Insulin After Treatment with Povidone-iodine Insulin was found to be higher in insulin-exposed skin of rat treated with P-I ointment, as compared to untreated insulin-exposed skin (Table III). This is also a support evidence for the "inactivation" reactions of intact insulin molecules by reducing agents in-vivo.

TABLE III

|  | insulin tissue level* |
| --- | --- |
| P-I treated skin | 1.00 IU/cm$^2$ |
| Untreated skin | 0.34 IU/cm$^2$ |

*Note: insulin tissue levels were determined by extraction with ethanol and analysis by HPLC assay.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A transdermal delivery system for treating diabetes and insulin influenced pathologic systemic conditions comprising insulin and a pharmaceutically acceptable oxidizing agent selected from the group consisting of permanganate and silver protein, said oxidizing agent enabling and facilitating the penetration of said active ingredient through the skin layers and into the blood stream.

2. A transdermal delivery system according to claim 1, wherein said insulin is incorporated into an adhesive patch.

3. A transdermal delivery system for treating diabetes and insulin influenced pathologic systemic conditions comprising insulin and buthionine sulfoximine.

4. A transdermal delivery system according to claim 1, further comprising a penetration enhancer.

5. A transdermal delivery system according to claim 4, wherein said penetration enhancer is oleic acid.

* * * * *

UNITED STATES PATENT AND TRADEMARK OFFICE
CERTIFICATE OF CORRECTION

PATENT NO. : 6,274,166 B1
DATED : August 14, 2001
INVENTOR(S) : Sintov et al.

It is certified that error appears in the above-identified patent and that said Letters Patent is hereby corrected as shown below:

<u>Title page,</u>
Item [73], Assignee, delete "(IL)" and insert -- (IL), part interest --, therefor.

Signed and Sealed this

Twenty-fourth Day of September, 2002

Attest:

Attesting Officer

JAMES E. ROGAN
Director of the United States Patent and Trademark Office